US00PP37662P2

(12) United States Plant Patent
Miyazaki et al.

(10) Patent No.: US PP37,662 P2
(45) Date of Patent: Sep. 1, 2026

(54) ***PETUNIA* PLANT NAMED 'Surf 271'**

(50) Latin Name: ***Petunia* x *hybrida***
Varietal Denomination: Surf 271

(71) Applicants: Kiyoshi Miyazaki, Hikone (JP); Yasuyuki Murakami, Higashiomi (JP)

(72) Inventors: Kiyoshi Miyazaki, Hikone (JP); Yasuyuki Murakami, Higashiomi (JP)

(73) Assignee: SUNTORY FLOWERS LIMITED, Tokyo (JP)

( * ) Notice: Subject to any disclaimer, the term of this patent is extended or adjusted under 35 U.S.C. 154(b) by 0 days.

(21) Appl. No.: 19/436,646

(22) Filed: Dec. 30, 2025

(51) Int. Cl.
*A01H 5/02* (2018.01)
*A01H 6/82* (2018.01)

(52) U.S. Cl.
USPC ..... Plt./356.21
CPC ..... *A01H 6/824* (2018.05)

(58) Field of Classification Search
USPC ..... Plt./356.21
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Petunia* plant named 'Surf 271', characterized by its compact, upright to outwardly spreading and eventually trailing plant habit; vigorous growth habit; freely branching habit; freely flowering habit; long flowering period; and single-type flowers with purplish pink-colored petals.

2 Drawing Sheets

Figure 1:
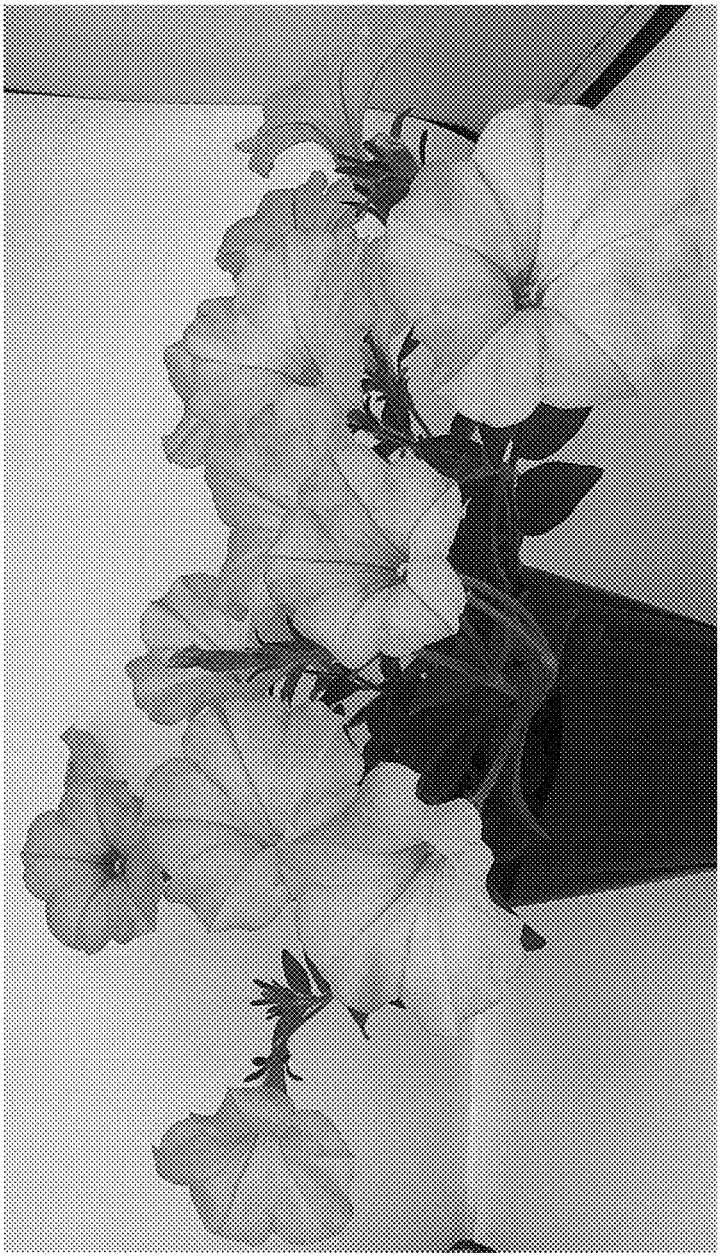

Botanical designation: *Petunia* x *hybrida*.
Cultivar denomination: 'SURF 271'.

BACKGROUND OF THE INVENTION

The present invention relates to a new and distinct cultivar of *Petunia* plant, botanically known as *Petunia* x *hybrida* and hereinafter referred to by the name 'Surf 271'.

The new *Petunia* plant is a product of a planned breeding program conducted by the Inventors in Higashiomi, Shiga, Japan. The objective of the breeding program is to create new outwardly spreading and freely-branching habit *Petunia* plants with numerous pink-colored flowers.

The new *Petunia* plant originated from a cross-pollination made by the Inventors in July, 2012 in Higashiomi, Shiga, Japan of a proprietary selection of *Petunia* x *hybrida* identified as code designation PV553, not patented, as the female, or seed, parent with a proprietary selection of *Petunia* x *hybrida* identified as code designation Px8317-2, not patented, as the male, or pollen, parent. The new *Petunia* plant was discovered and selected by the Inventors as a single flowering plant within the progeny of the stated cross-pollination in a controlled greenhouse environment in Higashiomi, Shiga, Japan in May, 2017.

Asexual reproduction of the new *Petunia* plant by terminal vegetative cuttings in a controlled greenhouse environment in Higashiomi, Shiga, Japan since April, 2023 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Surf 271'. These characteristics in combination distinguish 'Surf 271' as a new and distinct *Petunia* plant:

1. Compact, upright to outwardly spreading and eventually trailing plant habit.
2. Vigorous growth habit.
3. Freely branching habit.
4. Freely flowering habit.
5. Long flowering period.
6. Single-type flowers with purplish pink-colored petals.

Plants of the new *Petunia* can be compared to plants of the female parent selection. Plants of the new *Petunia* differ primarily from plants of the female parent selection in plant habit as plants of the new *Petunia* are more trailing than and not as mounding as plants of the female parent selection. In addition, plants of the new *Petunia* have smaller flowers than plants of the female parent selection.

Plants of the new *Petunia* can be compared to plants of the male parent selection. Plants of the new *Petunia* differ primarily from plants of the male parent selection in the following characteristics:

1. Plants of the new *Petunia* are more compact than and not as vigorous as plants of the male parent selection.
2. Plants of the new *Petunia* are more trailing than and not as mounding as plants of the male parent selection.
3. Plants of the new *Petunia* have larger flowers than plants of the male parent selection.

Plants of the new *Petunia* can also be compared to plants of the *Petunia* x *hybrida* 'Sunsurf Akatora', disclosed in U.S. Plant Pat. No. 23,970. In side-by-side comparisons, plants of the new *Petunia* and 'Sunsurf Akatora' differ primarily in the following characteristics:

1. Plants of the new *Petunia* are more compact than plants of 'Sunsurf Akatora'.
2. Plants of the new *Petunia* have larger flowers than plants of 'Sunsurf Akatora'.
3. Plants of the new *Petunia* and 'Sunsurf Akatora' differ in flower petal color as flower petals of plants of the new *Petunia* are purplish pink in color whereas flowers of plants of 'Sunsurf Akatora' have red-colored petals.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'Surf 271' grown in a container.

Figure 2:
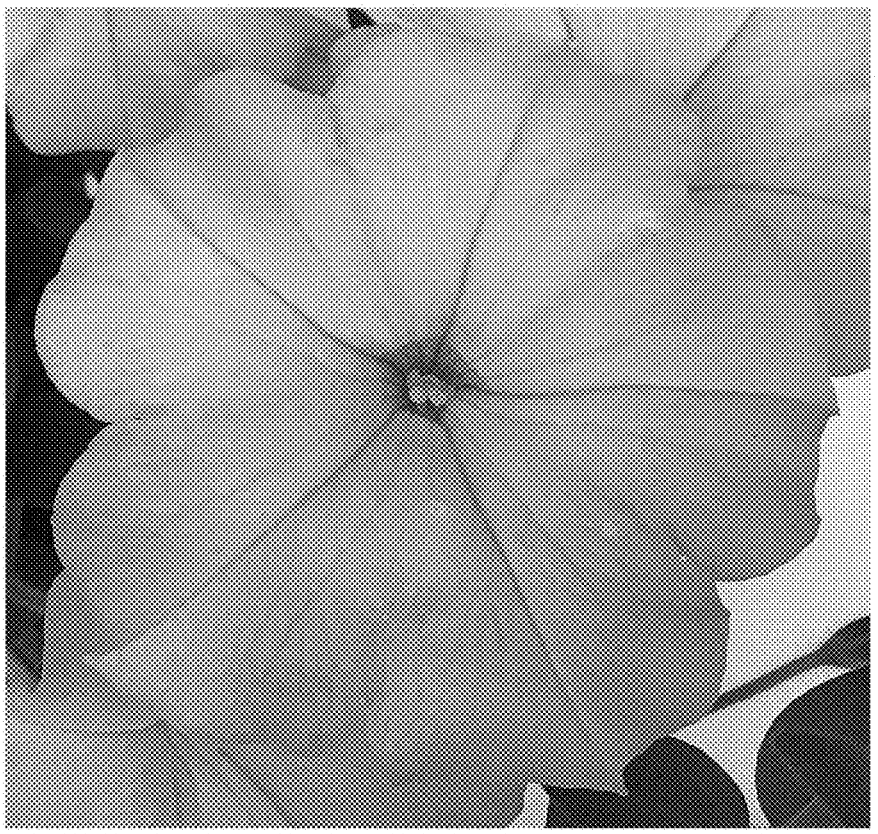

The photograph on the second sheet (FIG. 2) is a close-up view of a typical flower of 'Surf 271'.

DETAILED BOTANICAL DESCRIPTION

The aforementioned photographs and following observations, measurements and values describe plants grown during the spring in 24-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were six months old when the photographs and description were taken. In the following description, color references are made to The Royal Horticultural Society Colour Chart, 2015 Edition, except where general terms of ordinary dictionary significance are used.

Botanical classification: *Petunia* x *hybrida* 'Surf 271'.

Parentage:

*Female, or seed, parent*.—Proprietary selection of *Petunia* x *hybrida* identified as code designation PV553, not patented.

*Male, or pollen, parent*.—Proprietary selection of *Petunia* x *hybrida* identified as code designation Px8317-2, not patented.

Propagation:

*Type*.—By terminal vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color; actual color of the roots is dependent on substrate composition, water quality, fertilizer type and formulation, substrate temperature and physiological age of roots.

*Rooting habit*.—Freely branching; dense.

Plant description:

*Plant form and growth habit*.—Compact, upright to outwardly spreading and eventually trailing plant habit; freely branching habit with numerous lateral branches developing per plant; pinching enhances lateral branch development; vigorous growth habit.

*Plant height*.—About 16.2 cm.

*Plant diameter*.—About 30.2 cm.

Lateral branch description:

*Length*.—About 13.4 cm.

*Diameter*.—About 2.2 mm.

*Internode length*.—About 2.3 cm.

*Aspect*.—Upright to outwardly.

*Texture*.—Pubescent; rough.

*Color*.—Close to 144A.

Leaf description:

*Quantity and arrangement*.—About twelve leaves per lateral branch; alternate, simple.

*Length*.—About 4.4 cm.

*Width*.—About 2.7 cm.

*Shape*.—Ovate.

*Apex*.—Obtuse.

*Base*.—Attenuate.

*Margin*.—Entire.

*Texture, upper and lower surfaces*.—Sparsely pubescent; rough.

*Venation pattern*.—Pinnate; reticulate.

*Color*.—Developing leaves, upper surface: Close to 143A. Developing leaves, lower surface: Close to 144A. Fully expanded leaves, upper surface: Close to 138A; venation, close to 138B. Fully expanded leaves, lower surface: Close to 138B; venation, close to 144D.

*Petioles*.—Length: About 2 mm. Diameter: About 2.5 mm. Texture, upper and lower surfaces: Pubescent; rough. Color, upper and lower surfaces: Close to 138A.

Flower description:

*Flower arrangement and habit*.—Single-type salver-form flowers arising from upper leaf axils; freely flowering habit with usually about three flowers developing per lateral branch and numerous flower buds and flowers developing per plant during the flowering season; flowers face upright to outwardly.

*Fragrance*.—None detected.

*Natural flowering season*.—Early flowering habit; plants of the new *Petunia* initiate and develop flowers about three to four weeks after planting rooted young plants; long flowering period, flowering commences naturally during the spring and plants flower continuously throughout the summer and into the late autumn in Japan.

*Flower longevity*.—Individual flowers last about seven to ten days on the plant; flowers not persistent.

*Flower buds*.—Length: About 4.8 cm. Diameter: About 6.8 mm. Shape: Cylindrical. Color: Immature sepals, close to 137A; immature petals, close to 50D with venation, close to 146D.

*Flower diameter*.—About 7 cm.

*Flower tube length*.—About 3.5 cm.

*Flower tube diameter, distally*.—About 1.4 cm.

*Flower tube diameter, proximally*.—About 3.7 mm.

*Corolla*.—Quantity and arrangement: Five petals in a single whorl, fused at the base and opening into a flared trumpet. Petal length from throat: About 3.3 cm. Petal width: About 3.4 cm. Petal shape: Roughly spatulate. Petal apex: Cuspidate. Petal margin: Entire; slightly undulate. Petal texture, upper and lower surfaces: Smooth, glabrous. Throat texture: Smooth, glabrous. Tube texture: Pubescent. Color: Petal lobe, when opening, upper surface: Close to 73B and 73C. Petal lobe, when opening, lower surface: Close to 73D. Petal lobe, fully opened, upper surface: Close to 73C; venation, close to 152D. Petal lobe, fully opened, lower surface: Close to 146D; venation, close to 146D. Throat: Distally and mid-section, close to 145D; proximally, close to 145B; venation, close to N148C. Tube: Distally and mid-section, close to 69C; proximally, close to 149D; venation, close to 146D.

*Calyx*.—Arrangement: One star-shaped calyx tube with five sepals arranged in a single whorl and fused at the base. Sepal length: About 1.3 cm. Sepal width: About 2.7 mm. Sepal shape: Linear. Sepal apex: Acute. Sepal margin: Entire. Sepal texture, upper and lower surfaces: Pubescent; rough. Color, upper surface: Close to 137A. Color, lower surface: Close to 138A.

*Peduncles*.—Length: About 3.5 cm. Diameter: About 1.4 mm. Aspect: Upright to outwardly. Texture: Pubescent; rough. Color: Close to 143C.

*Reproductive organs*.—Stamens: Quantity per flower: Five. Filament length: About 1.3 cm. Filament color: Close to 155D. Anther shape: Ellipsoidal. Anther size: About 1.4 mm by 1.6 mm. Anther color: Close to 8D. Pollen amount: Moderate. Pollen color: Close to 8D. Pistils: Quantity per flower: One. Pistil length: About 2.6 cm. Style color: Close to 138C. Stigma shape: Transversely ellipsoidal. Stigma color: Close to 150D. Ovary color: Close to 138A. Seeds and fruits: To date, seed and fruit development have not been observed on plants of the new *Petunia*.

Temperature tolerance: Plants of the new *Petunia* have been observed to tolerate temperatures ranging from about 5° C. to about 35° C.

Pathogen & pest resistance: To date, plants of the new *Petunia* have not been observed to be resistant to pathogens and pests common to *Petunia* plants.

It is claimed:

1. A new and distinct *Petunia* plant named 'Surf 271' as herein illustrated and described.

* * * * *